United States Patent [19]

Lewin et al.

[11] 4,303,077
[45] Dec. 1, 1981

[54] DEVICE FOR THE MEASUREMENT OF THE LOCATION, THE POSITION AND/OR THE CHANGE OF LOCATION OR OF POSITION OF A RIGID BODY IN SPACE

[75] Inventors: Arthur Lewin, Johannesburg, South Africa; Bernd Nickel, Bensheim, Fed. Rep. of Germany

[73] Assignee: Siemens Aktiengesellschaft, Berlin & Munich, Fed. Rep. of Germany

[21] Appl. No.: 25,263

[22] Filed: Mar. 29, 1979

[30] Foreign Application Priority Data

Apr. 4, 1978 [DE] Fed. Rep. of Germany ....... 2814551

[51] Int. Cl.³ .......................... A61B 5/05; A61B 5/10
[52] U.S. Cl. ...................................... 128/777; 433/69
[58] Field of Search ............... 128/653, 782, 774, 777, 128/765, 776, 1.3, 775; 433/68, 69; 310/DIG. 3; 338/32 H; 323/94 H; 324/251, 252, 208, 247

[56] References Cited

U.S. PATENT DOCUMENTS

| | | | |
|---|---|---|---|
| 3,439,358 | 4/1969 | Salmons | 128/653 |
| 3,528,402 | 9/1970 | Abramowitz | 128/653 |
| 3,822,694 | 7/1974 | Mills | 128/653 |
| 4,197,855 | 4/1980 | Lewin | 128/653 |

FOREIGN PATENT DOCUMENTS

| | | | |
|---|---|---|---|
| 1013880 | 6/1960 | Fed. Rep. of Germany | 128/653 |
| 1931004 | 1/1970 | Fed. Rep. of Germany | 128/777 |
| 182854 | 8/1966 | U.S.S.R. | 128/777 |
| 232447 | 4/1969 | U.S.S.R. | 128/777 |

Primary Examiner—Robert W. Michell
Assistant Examiner—John E. Hanley
Attorney, Agent, or Firm—Hill, Van Santen, Steadman, Chiara & Simpson

[57] ABSTRACT

In an exemplary embodiment, a magnetic field generator is arranged directly on the body or at an interval therefrom, and is designed in such manner that it generates a defined irregular field. For determining the field flux, a plurality of magnetic flux pick-ups with magnetic flux-dependent sensor elements are arranged on a carrier at an interval from one another in at least two, preferably in three, planes which stand perpendicular to one another. Moreover, the arrangement is executed in such manner that a free space is formed between the magnetic flux pick-ups corresponding to the intervals therebetween. The device is suited in particular for employment in dental medicine, and, namely, for the determination of lower jaw movements in a patient.

15 Claims, 6 Drawing Figures

DEVICE FOR THE MEASUREMENT OF THE LOCATION, THE POSITION AND/OR THE CHANGE OF LOCATION OR OF POSITION OF A RIGID BODY IN SPACE

BACKGROUND OF THE INVENTION

The invention relates to a device for the measurement and registration of the location, the position and/or the change of location or position of a rigid body in space upon employment of a field generator, preferably a magnetic field generator, arranged directly on the body or at an interval therefrom, with means independent of the body arranged at an interval from the field generator for determining the field flux or, respectively, the field flux change during a measurement, as well as with an electronic installation for the production and evaluation of electric signals arising upon a field flux or, respectively, a field flux change.

In the earlier German patent application No. P 27 15 106 (U.S. Pat. No. 4,197,855 issued Apr. 15, 1980), a device of the said type was proposed in which, for the determination of the field flux, a plurality of surface pairs arranged perpendicularly to one another are provided, whereby each surface pair contains a multitude of sensor elements.

The arrangement of such a surface structure is relatively bulky and heavy and, particularly upon employment in dental medicine, has the disadvantage when determining the exact position or, respectively, a change of position of a point of the lower jaw of a patient that the access to the mouth area of the patient is obstructed and, therefore, the introduction of chewing matter for a measurement of the chewing motion is rendered more difficult.

It has further become apparent that the signals which give information for a rotational movement are relatively small in this arrangement and, thus, difficult to evaluate, particularly when the magnetic field generator is located in the center of the pick-up system, because the differential signals are already very small here. The formation of further differential signals from the differential signals received leads to even smaller signals which, as a result of the background noise of the electronic system which is already present and cannot be avoided, can be evaluated only relatively poorly and imprecisely.

Moreover, in order to compensate the influence of the earth's magnetic field in this arrangement, a compensation circuit for the three planes of the field pick-ups is required which necessitates an additional circuit-technical outlay.

SUMMARY OF THE INVENTION

The object of the invention is to create an improved device which, particularly as seen in terms of the construction, is lighter and thus can be more favorably mounted at a measuring location, which delivers signals which can be better evaluated, and which creates an improved access to the area of the field generator. A further goal of the invention is to simplify the electronics for the production of the signals, in particular with respect to the cable and line guidance.

The object set up is inventively achieved in a device of the type initially cited in that the field generator is designed in such manner that it generates a defined irregular field; in that, for determining the field flux, a plurality of magnetic flux pick-ups with magnetic flux-dependent sensor elements are arranged at a distance from one another on a support, preferably in three planes which are perpendicular to one another, and the arrangement is undertaken in such manner that a free space is formed by the distance between the magnetic flux pick-ups.

Advantageous further developments and embodiments of the invention are stated in the subclaims.

A large-surfaced and bulky structure is avoided by means of the specific design and arrangement of the magnetic flux pick-ups for determining the magnetic flux or, respectively, a change of magnetic flux. The entire pick-up arrangement is thereby significantly lighter and easier to manipulate. It is particularly advantageous for employment in dental medicine for determining the exact position or, respectively, a change of position of a location in the lower jaw of a patient. By means of the free space, which can be achieved by means of the magnetic flux pick-ups arranged at intervals, the access to the magnetic field generator is improved and, thus, the fixing and securing of the same as well as—upon employment in dental medicine—the dispensing of chewing matter to the patient is facilitated. A further significant advantage is that no additional outlay for a compensation circuit for avoiding an influence of the earth's magnetic field is required. By means of the arrangement of a multiplex connection unit in the area of the magnetic flux pick-up arrangement, the plurality of the lines can be significantly reduced, so that only a relatively thin connection cable is required from the pick-up system to the electronics.

By means of the arrangement of the magnetic field generator and the magnetic flux pick-ups, one succeeds in picking up all movements of the body, i.e. both the translational as well as the rotational movements, with only six pick-ups.

A sample embodiment of the invention is explained in greater detail on the basis of FIGS. 1 through 6; and other objects, features and advantages will be apparent from this detailed disclosure and from the appended claims.

DETAILED DESCRIPTION

Figure 1:
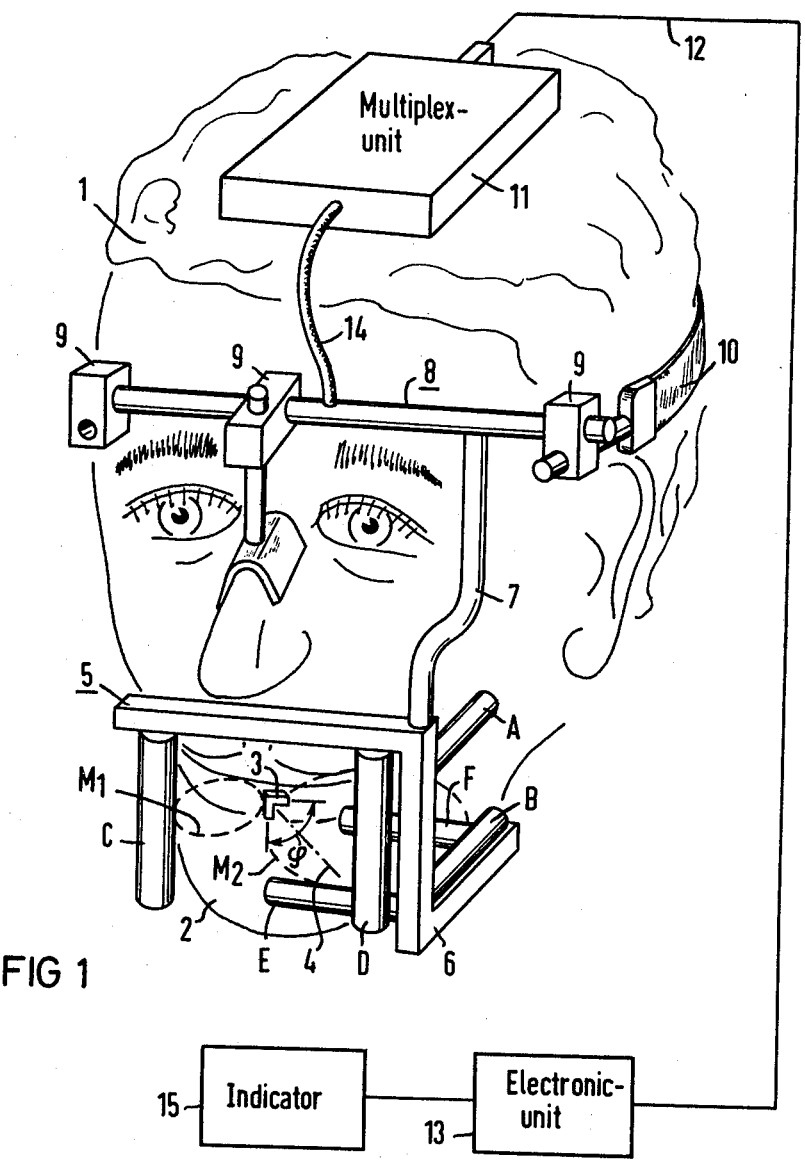
FIG. 1 is a diagrammatic perspective illustration, showing the inventive measuring device employed in dental medicine in association with the lower jaw of a patient, and schematically illustrating associated electric circuit components.

FIG. 1, in a diagrammatic and schematic illustration, shows the inventive measuring device employed in dental medicine for the determination of the location, the position and/or of a change of location or of position of a point at the lower jaw of a patient. In FIG. 1, the head is referenced with 1 and the lower jaw of a patient is referenced with 2. A permanent magnet serving as the field generator is referenced with 3, which permanent magnet can be secured intraorally at any desired location of the lower jaw by means of suitable bonding or adhesive agents (for example impression mask). The magnetic field generator 3 consists of two uniformly dimensioned bar magnets as are described in greater detail in the German patent application No. P 27 15 106, however, with the difference that the aperture angle $\phi$ amounts to approximately 90°, and in any event is less than 180° and preferably between 80° and 120°. The bar magnets of the magnetic field generator 3 are relatively small; they have a length of about 3 mm and a cross section of 1 mm square. The angle bisector of the two bar magnets is referenced with 4. The magnetic field generator 3 generates two magnetic fields $M_1$, $M_2$ indicated in the Figure with broken lines, and, namely, a relatively small resultant field $M_1$ at the point of contact of the like poles (for example N-N) and a relatively large resultant field $M_2$ at the free legs.

A magnetic flux pick-up arrangement 5 which contains six bar-shaped magnetic flux pick-ups A through F which are secured to a carrying frame 6 is arranged extraorally. The carrying frame 6 is connected with a carrying rod 7 which in turn is secured to rods 8 designed as a spectacle or head mount. The rods 8 contain a number of joints 9 which render possible an adaptation and adjustment of the entire device to the patient upon whom a measurement is to be undertaken. In order to be able to fix the entire rod system securely on the head 1 of the patient, a fastening strap 10 is laid around the head of the patient.

The arrangement of the magnetic field generator 3 and the magnetic field pick-ups A through F is executed in such manner that the angle bisector 4 about bisects the vertical part of the carrying frame 6. Moreover, the magnetic flux pick-up C is displaced outward to such a degree that the resultant magnetic field $M_2$ generated by the magnetic field generator which proceeds from the free ends of the two bar magnets is only picked up by the antennas A, B, D, E and F and the significantly smaller resultant magnetic field $M_1$ proceeding from the ends of the bar magnets abutting one another with their like poles is essentially only picked up by the magnetic flux pick-up C.

A multiplex unit designed for mounting on the head of the patient is referenced with 11 and will be explained in greater detail later; it is connected via a connection cable 12 with an electronic unit 13 on the one hand and via a cable 14 with sensor elements arranged in the magnetic flux pick-ups A through F on the other hand. The output of the electronic unit 13 is connected to an indicator 15 known per se, at which the detected and evaluated signals are optically displayed.

The magnetic flux generator 3 is secured in the patient's mouth in such manner that the one leg proceeds approximately parallel to a plane formed by the pick-ups E and F and the other leg proceeds approximately parallel to a plane formed by the pick-ups C and D, whereby the aperture of the magnetic field generator (angle bisector 4) is directed toward the pick-ups, so that pick-ups A, B, D, E, and F are influenced by the magnetic flux of resultant magnetic field $M_2$.

Figure 2:
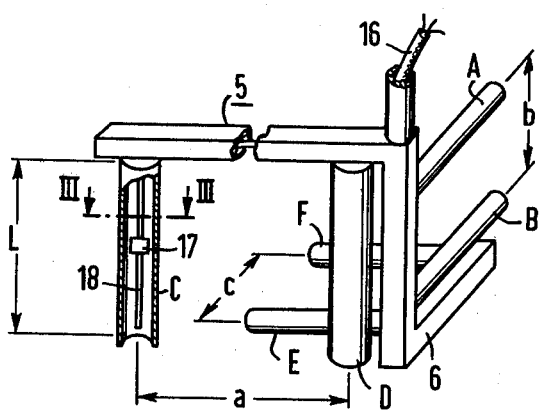
FIG. 2 is a partial somewhat diagrammatic perspective view showing the magnetic flux pick-up arrangement of FIG. 1, and with certain parts broken away and in section to show interior construction.

FIG. 2 shows the magnetic flux pick-up arrangement 5 with the magnetic flux pick-ups A through F, and wherein the magnetic flux pick-up C is illustrated in cross section. It can be seen from the illustration that the magnetic flux pick-ups are respectively mounted in pairs on the carrying frame 6, whereby the magnetic flux pick-ups of each pair are arranged in a plane and at an interval a, b, c to one another. The frame 6 is designed ⌐-shaped, whereby the two free legs of the frame are angled, and thus lie in two planes disposed perpendicular to one another, and consists of a hollow section in which signal and supply line 16 lead to and from the individual magnetic flux pick-ups A through F. The magnetic flux pick-ups A through F each include a nonmagnetic hollow tube (e.g. 19, FIG. 3) which incorporates a Hall generator 17 serving as a sensor element as well as a respective antenna (or field-interactive) bar 18 at the interior of the tube. The antenna bar 18 is arranged facing the magnetic field generator and respectively consists of Mumetal magnetic material. It respectively extends over the entire length of a magnetic flux pick-up. The Hall generator 17 is arranged with its longitudinal midpoint at about half the length of the antenna bar. The intervals a, b, c and the respective length L of the magnetic field pick-ups A through F each of which may have the configuration of the antenna 18, are determined by the motion range of the object to be measured (lower jaw).

Figure 3:
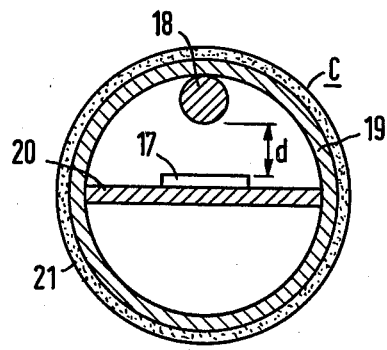
FIG. 3 is a somewhat diagrammatic enlarged horizontal sectional view taken along the line III—III of FIG. 2 and showing details concerning the construction of the magnetic flux pick-up elements.

FIG. 3, which shows a cross section along the line III—III in FIG. 2, reveals further details concerning the construction of the magnetic flux pick-ups.

The magnetic flux pick-up C, like the remaining pick-ups A, B and D through F, essentially consists of a tube 19 of about 9 mm exterior diameter, of a support plate 20 for the Hall generator 17 arranged in the tube 19, of the Hall generator 17 and of the antenna bar 18 secured to the tube 19. A conforming protective elastic casing 21, for example, of foam elastic material, is arranged around the tube 19 for enclosing the same. The tube 19 consists of a non-ferromagnetic material, for example, of aluminum. The Hall generator 17 is designed lamina-like and is arranged with its effective surface at an interval d from the antenna bar 18 in such manner that the bar axis forms an equilateral triangle with the exterior edges of the lamina upon top view of the Hall generator (as viewed in FIG. 3), the height of the equilateral triangle corresponding to interval d plus the radius of bar 18.

The employment of Mumetal bars (about 1.5 mm diameter in the present sample embodiment) as antenna bars 18 and the suitable selection of the interval d of about 3.5 mm lead to a linearized characteristic of the Hall generators 17, whereby the voltages at the Hall generators do not change over the entire length of the Mumetal bars. Because of this arrangement, one receives linearized signals (See the mathematical discussion which follows.)

As already indicated in FIG. 2, the lines 16 proceeding from the Hall generators 17 to the multiplex unit 11 (FIG. 1) proceed in the inside of tubes 19, of the carrying frame 6 and the carrying rod 7.

Figure 4:
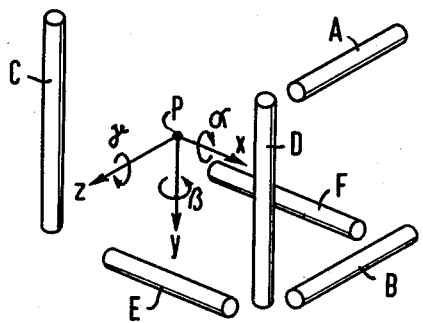
FIG. 4 is a diagrammatic view showing the arrangement of the magnetic flux pick-up elements in relation to a coordinate system whose origin corresponds to the assumed position of the magnetic field generator as shown in FIG. 1.

In schematic representation, FIG. 4 again shows the arrangement of the magnetic flux pick-ups A through F and the signals x, y and z for representing the components of a translational movement and α, β and γ for a rotational movement which can be received in the three planes of the space from a reference point P which corresponds to an assumed position of the magnetic field generator 3 in an initial position.

From that arrangement, the following relationship is derived for the output signals (direct current signals) at the magnetic flux pick-ups or, respectively, Hall generators:

| A = x + y + α | C = z + y + γ | E = y + z + β |
|---|---|---|
| B = x − y − α | D = z − y − γ | F = y − z − β |

There derives from the mathematical relationship A+B that the sum of the signals at the pick-ups A and B is a measure for the pure translational movement in the direction of the x-axis.

From the equation $$A+B=2\cdot x \tag{I}$$

a translational movement in the direction of the x-axis can therefore be measured.

The difference of the signals A, B, i.e. A−B, yields a mixture of translational movement in y-direction and rotational movement around α.

$$A-B=2(y+\alpha)$$

By analogy, the following relationship is valid for the pick-ups E and F:

$$E+F=2\cdot y \tag{II}$$

The difference of the signals E, F, i.e. E−F, again produces a mixture of translational movement in x-direction and rotational movement around $$E-F=2\cdot(x+\beta)$$

From the equation $$(A-B)-(E+F)=2y+2\alpha-2y=2\alpha \tag{III}$$

one receives the signal α as a measure for the rotation around the y-axis.

The corresponding case derives for a movement in the direction of the z-axis.

From the equation $$C+D=2\cdot z \tag{IV}$$

one thus obtains the signals z as a measure for the translation in z-direction.

The difference of the signals C−D again produces a mixture of translational movement in y-direction and rotational movement around $$C-D=2\cdot(y+\gamma)$$

From the equations $$(A+B)-(E-F) \tag{V}$$

and $$(C-D)-(E+F) \tag{VI}$$

one obtains the signals β and γ as a measure for the rotational movement around the y- and z-axes.

Figure 5:
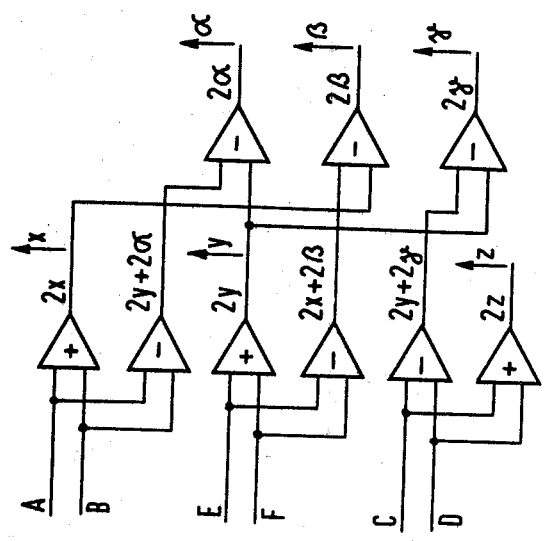
FIG. 5 is a block diagram indicating how the output signals are obtained from the signals supplied by the respective magnetic flux pick-up elements arranged as shown in FIG. 4.

When, therefore, the output signals are linked with one another corresponding to the block diagram in FIG. 5, then one succeeds in receiving the rotational and translational signals separated from one another.

Figure 6:
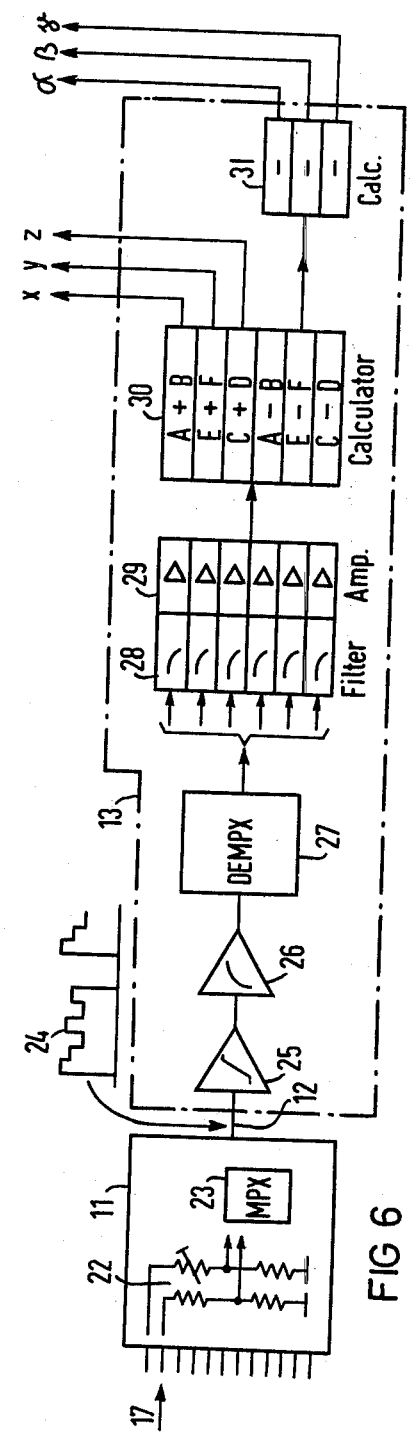
FIG. 6 shows a schematic block diagram for explaining the signal processing carried out by the multiplex unit and the electronic unit of FIG. 1.

FIG. 6, on the basis of a block diagram, shows the signal processing proceeding from the multiplex unit 11, whereby two lines lead from each magnetic flux pick-up A–F or in particular from each Hall generator 17 to the multiplex unit 11.

A bridge balance circuit 22 is present in the multiplex unit 11 for each Hall generator 17. The bridge balance circuit 22 serves to compensate electric asymmetries which are conditioned by production engineering. The signals (direct current signals) derived from the six Hall generators are subsequently coded in a time-division multiplex unit 23 in a specific pulse sequence, which is indicated by means of the illustration 24. The pulse sequence 24 is then supplied via the line 12 to the electronic unit 13, namely first to a preamplifier 25, then to a linearization amplifier 26, to a demultiplex circuit 27, subsequently to a filter 28 and a further amplifier 29 and, finally, to a calculator 30 and a calculator 31. Finally, analogous to the linkage revealed in FIG. 5, the calculator 30 delivers the individual signals for the translational movement and the calculator 31 delivers the individual signals for the rotational movement.

It will be apparent that many modifications and variations may be effected without departing from the scope of the novel concepts and teachings of the present invention.

We claim as our invention:

1. Device for the measurement and registration of the location, the position and/or the change of location or position of a rigid body in space, said device comprising a magnetic field generator for generating a field comprising magnetic field flux and for mounting in fixed relation to the body, sensing means for determining the magnetic field flux or the magnetic field flux change during a measurement operation, said sensing means being arranged at a distance from the magnetic field generator and being mounted independently of the magnetic field generator, and an electronic installation coupled with said sensing means for the production and evaluation of electric signals in accordance with magnetic field flux or a magnetic field flux change, said magnetic field generator (3) being designed in such manner that it generates a defined irregular field; said sensing means being operable for determining the magnetic field flux in at least two planes disposed mutually perpendicularly to one another and comprising a plurality of pairs of magnetic flux pick-ups (A/B; C/D; E/F) with magnetic flux-dependent sensor elements (17), and support means mounting the respective magnetic flux pick-ups of the respective pairs at respective intervals (a, b, c) from one another and in such a manner that a free space is formed between the respective magnetic flux pick-ups of the respective pairs by means of the respective intervals (a, b, c), a pair of said magnetic flux pick-ups (A/B; C/D; E/F) being arranged in each of said planes, and each of the magnetic flux-dependent sensor elements being a Hall generator (17) with a longitudinal axis of symmetry, and each of said magnetic flux pick-ups further comprising a field-interactive element (18) arranged at the side of the Hall generator (17) toward the magnetic field generator (3), and having a longitudinal axis parallel to the longitudinal axis of symmetry of the Hall generator (17) and spaced at an interval (d) from said longitudinal axis of symmetry of the Hall generator (17), so that the Hall generators of the respective magnetic flux pick-ups provide linearized signals independent of relative movement between the magnetic field generator and the sensing means parallel to the longitudinal axes of the respective field-interactive elements.

2. Device according to claim 1, with said elements of each magnetic flux pick-up (A–F) being in the form of an elongated bar (18) having a length (L) in the direction of the longitudinal axis of the bar, having a midpoint in said length (L) and having a center of a cross section thereof as viewed at right angles to said longitudinal axis, the Hall generator (17) of each magnetic flux pick-up having outer edges disposed generally parallel to the longitudinal axis of symmetry of such Hall generator (17), and each Hall generator (17) having a longitudinal midpoint opposite the midpoint in the length (L) of the bar (18) and being arranged in such manner that viewed in a plane at right angles to the length of the bar (18), the outer edges of the Hall generator (17) form an equilateral triangle with the center of the cross section of the bar (18).

3. Device according to claim 2, with each bar (18) being of mumetal.

4. Device according to claim 1, with each magnetic flux pick-up further comprising a tube-shaped carrier (19) of nonferromagnetic material, the Hall generator (17) and the element (18) of each magnetic flux pick-up being fixed in the tube-shaped carrier (19) of such magnetic flux pick-up.

5. Device according to claim 4, with each magnetic flux pick-up further comprising a soft conforming elastic casing (21) surrounding the tube-shaped carrier (19) of such magnetic flux pick-up.

6. Device according to claim 1, with said support means for the respective magnetic flux pick-ups comprising a generally Z-shaped carrying frame (6) having legs extending at right angles to one another and which frame being at least partially hollow to provide hollow spaces, and electric lines (16) leading to and from the Hall generators (17) and extending in the hollow spaces of the frame.

7. Device according to claim 1, with said magnetic field generator comprising two bar magnets (3) having adjacent ends with like poles (for example, N-N) which abut and which bar magnets extend in different directions and have respective free ends providing free poles, said bar magnets (3) having an angle ($\phi$) between the bar magnets smaller than 180°, and means comprising the spatial arrangement of the magnetic flux pick-ups (A through F) with reference to the magnetic field generator (3) such that one pick-up (C) is essentially influenced by the magnetic flux ($M_1$) which proceeds from the abutting poles of the field generator (3) and the remaining pick-ups (A, B, D, E, F) are influenced by the magnetic flux ($M_2$) which proceeds from the free poles of the field generator (3).

8. Device according to claim 1, with said electronic installation having means forming sum and differential signals from respective linearized signals produced from the Hall generators (17) of each pick-up pair (A/B; C/D; E/F), which sum and differential signals supply discrete individual signals for the calculation of translational and rotational motion of said generator relative to said sensing means.

9. Device according to claim 8, with said electronic installation having processing means for processing the sum and differential signals according to $$(A-B)-(E+F)=2\alpha$$

$$(A+B)-(E-F)=2\beta$$

$$(C-D)-(E+F)=2\gamma$$

where (A+B) and (A−B) represent the sum and difference of the linearized signals from one pair of pick-ups (A/B) lying in one plane, (C+D) and (C−D) represent the sum and difference of linearized signals from a second pair of pick-ups (C/D) lying in a second plane, (E+F) and (E−F) represent the sum and difference of linearized signals from a third pair of pick-ups (E/F) lying in a third plane, x, y, z represent translational motion along coordinate axes of respective first, second and third planes, and $\alpha$, $\beta$, $\gamma$ represent rotational motion about respective coordinate axes x, y, z.

10. Device according to claim 8, with said electronic installation comprising a multiplex unit (11) with a multiplex circuit arrangement (23) which converts the signals derived from the magnetic flux pick-ups (A through F) into a coded pulse sequence (24); and a demultiplex circuit arrangement (27) which decodes the pulse sequence (24) into individual signals.

11. Device according to claim 10, with said multiplex unit (11) including a bridge balance circuit (22) for each magnetic flux pick-up (A through F).

12. Device according to claim 1, for measurement and registration of the location, the position and/or of the change of location or of position of a location of the lower jaw of a patient in dental medicine, with said magnetic field generator (3) being fixed relative to such location of the lower jaw.

13. Device according to claim 12, with said support means for the magnetic flux pick-ups (A through F) comprising a carrying frame (6), and a head mount (8) for mounting on the head of a patient and operatively supporting said carrying frame (6) in such a manner that the free space between the magnetic flux pick-ups provides access to the mouth of the patient.

14. Device according to claim 13, with said head mount (8) having a plurality of joints (9) for adaptation to the patient's head (1).

15. Device according to claim 10, with a mount (8) disposed on the head (1) of a patient, and said multiplex unit (11) being designed for association with said mount on the head of the patient.

* * * * *